United States Patent [19]

Gerstein

[11] Patent Number: 5,139,771
[45] Date of Patent: Aug. 18, 1992

[54] RINSE AWAY FACE MASQUE
[75] Inventor: Terry Gerstein, East Brunswick, N.J.
[73] Assignee: Revlon, Inc., New York, N.Y.
[21] Appl. No.: 835,028
[22] Filed: Feb. 11, 1992

Related U.S. Application Data

[63] Continuation of Ser. No. 509,113, Apr. 16, 1990, abandoned.

[51] Int. Cl.$^5$ ............................................. A61K 7/00
[52] U.S. Cl. ................................... 424/63; 424/195.1; 424/196.1; 424/401; 514/778; 514/779; 514/782; 514/844
[58] Field of Search ............ 424/63, 196.1, 195.1, 424/401; 514/778, 779, 782, 844

[56] References Cited

U.S. PATENT DOCUMENTS

| | | | |
|---|---|---|---|
| 3,258,398 | 6/1966 | Doell | 167/58 |
| 3,850,838 | 11/1974 | Guckenberger | 132/7 |
| 3,894,880 | 7/1975 | Colgrove | 106/208 |
| 4,000,317 | 12/1976 | Menda | 424/357 |
| 4,126,142 | 11/1978 | Saute | 132/7 |
| 4,369,173 | 1/1983 | Causland | 424/35 |
| 4,391,799 | 7/1983 | Mason | 424/132 |
| 4,393,048 | 7/1983 | Mason | 424/132 |
| 4,524,064 | 7/1985 | Nambu | 424/81 |
| 4,650,670 | 6/1987 | Callingham | 424/65 |
| 4,818,751 | 4/1989 | Ibe | 514/54 |
| 4,826,809 | 5/1989 | Giesen | 514/2 |
| 4,847,074 | 7/1989 | Hatae | 424/62 |
| 4,994,264 | 2/1991 | Verdon et al. | 424/63 |

*Primary Examiner*—Thurman K. Page
*Assistant Examiner*—Amy Hulina
*Attorney, Agent, or Firm*—Julie Blackburn

[57] ABSTRACT

A face masque composition useful for treating human skin for improvement comprising about 1-70% of a hydrolzed grain endproduct, about, 0.1-15% of a seaweed derivative and about 20-95% water.

9 Claims, No Drawings

RINSE AWAY FACE MASQUE

This is a continuation of copending application(s) Ser. No. 07/509,113 filed on Apr. 16, 1990 now abandoned.

TECHNICAL FIELD

The invention is directed to a composition containing hydrolyzed grain endproducts of maltodextrin or corn syrup solids, and seaweed derivatives which composition is used as a face masque for human skin.

BACKGROUND OF INVENTION

Face masques are skin treatment products which produce a variety of favorable results for the user. There are two general categories of face masques: a peel-off type and a rinse-away type. Both types require that a film coating be formed to contour the face. The peel-off type is removed by physically peeling the film away from the face and the rinse-away type is removed by thorough rinsing with tap water.

The major function of most masques is to deep clean facial skin by removing dead skin cells. Masques may also improve capillary blood circulation, cleanse, retexturize, firm and moisturize as well as stimulate the skin and increase cell regeneration. Moreover, masques tone the skin as would a muscle and their employment can be considered a beneficial exercise for the face in which the indulger hopes to gain a more youthful appearance.

Most rinse-away masques contain special ingredients which can influence the masque's method of employment. "Homemade" masks prepared from household ingredients have been used long before the introduction of modern commercial cosmetic masques. Homemade masks usually employ special ingredients based upon fruit or vegetables, for example cucumber masks, strawberry masks and honey masks are not uncommon. A recipe for an apple mask claims that apples can refresh and rejuvenate the skin and suggests: "cook one peeled and cored apple in a small amount of milk, mash together and apply the mixture." Homemade masks are based upon the virtues of natural ingredients which are judged to be wholesome, healthful, safe and beneficial to the skin. Homemade masks have several disadvantages, however. They are time consuming to prepare, their effects are somewhat limited and questioned, they can vary considerably from preparation to preparation according to the expertise of the cook-formulator, and they have to be remade for each new application since they spoil if stored. Moreover, homemade masques do not have the cosmetic elegance necessary for modern cosmetic face treatment products. Today's products differ from the "old-fashioned" masques by their improved cosmetic elegance, their convenience, their attribute of "deep" cleansing and the sensuous effects which they impart to skin.

Some cosmetic face masques have been adapted from moisturizing creams. Here, heavy aqueous emulsions, laden with mineral oils, esters, triglycerides and waxy materials, are applied to the face in the form of an opaque emollient coating. As the cream remains on the face water evaporates imparting a cooling sensation to the skin. After 10 or 15 minutes the cream is rinsed off the face leaving the skin looking clean and feeling hydrated, soft and smooth.

In addition to hydrophobic ingredients, masques may contain surfactants, preservatives, fragrance, colorants and special ingredients such as botanicals which enhance therapeutic and cosmetic properties.

Clay or mud masques are also popular and based upon the absorptive nature of inorganic clays or "muds". The clay ingredients generally employed in contemporary cosmetic masks are bentonite, kaolin, montmorillonite, or mixtures thereof. They may be supported by other inorganics such as alumina and talc, and may be optionally colored earthtone with iron oxide. These materials are formulated into aesthetic products using an array of conventional ingredients such as wetting, suspending and dispersing surfactants, hydrocolloid thickeners, preservatives, fragrance, and so on.

Clay face masques permit deep cleansing of the skin due to the absorptive properties of the clay raw materials. After applying a clay masque to the face it dries and cools because of the evaporation of the aqueous vehicle. The masque contracts producing a tightening sensation on the skin, an astringency. As it dries, it hardens and the iron pigments, which produce earthtone shades, change color giving an additional visual effect. After hardening is completed, or near complete as specified by product directions, the masque is rinsed away with water. The face is left feeling relieved of constraint and totally refreshed.

Sometimes special organic ingredients are added to face masques, for example high molecular weight synthetic polymers which help film formation, or powdered egg white whose aqueous film is known to produce skin like coatings which are astringent during drying. Unless ingredients like egg white are used at high concentrations to give specific and perceptible effects their use in masque formulas is merely promotional. However, promotional ingredients do play an important role not only in masques but in all cosmetic formulas because they capture the fancy of the consumer and induce purchase of the product. After purchase and after application the inherent properties and benefits of the masque will determine if the consumer will repurchase the product.

Although the advantages of contemporary cosmetic face masques are quite demonstrable, there are a number of disadvantages associated with them as well:

Emollient masques are greasy and can stain towelling and clothing if not carefully applied.

Clay masks are messy during application and during rinse-off. They can soil bathroom appointments with heavy and colored muds.

All masques can be embarrassingly funny looking. They place the face in an artifical cast. An unnatural appearance during employment of the masque can startle if not frighten a passerby who unintentionally intrudes.

Masque employment requires patience. They dry slowly, requiring 10, 15 or more minutes before rinse-off. The prolonged time may be discomforting to the user since masques tend to harden and shrink on the face.

Masques generally are non-routine face treatments, lending themselves to use somewhat infrequently. Some masques, however, can be used several times a week but are hardly ever recommended for daily application.

Some masques do not satisfy the user's total objective. They provide limited improvement of facial skin, they may have disagreeable side-effects such as acting harshly on the skin; they may not cleanse satisfactorily, or they may not provide sufficient sensuous effect. In brief, modern cosmetic face masque technology has come a long way from old fashioned homemade masks but they have much to gain in future improvement.

SUMMARY OF INVENTION

The invention is directed to a face masque composition used to impart improved properties to human skin comprising about 1-70% of a hydrolyzed grain endproduct, about 0.1-15% of a seaweed derivative and about 20-95% water.

The invention is a also directed to a method for treating human skin for improvement comprising administering to the facial skin a face masque composition comprised of about 1-70% of a hydrolyzed grain endproduct, about 0.1-15% of a seaweed derivative, and about 20-95% water.

DETAILED DESCRIPTION

It has been discovered that by combining two natural polysaccharides a superior rinse-away face masque which is free of the many disadvantages that are associated with contemporary cosmetic masques can be obtained.

The face masque composition of the invention comprises about 1-70% of a hydrolyzed grain endproduct which is maltodextrin or corn syrup solids. Maltodextrins tend to be highly water soluble glucose polymers obtained from the reaction of starch with acid and/or enzymes in the presence of water. The ensuing hydrolysis results in a carbohydrate mixture of various saccharides with a Dextrose Equivalence (DE) of less than 20. Corn syrup solids are produced by a similar process but have a DE of 20 or higher. Dextrose Equivalence is a measure of the degree of starch polymer hydrolysis determined by quantitative analysis. It is defined as reducing sugars expressed as dextrose and reported as a percentage of the dry substance. The United States Food and Drug Administration (F.D.A.) defines maltodextrins, $(C_6H_{10}O_5)_n \bullet H_2O$, as nonsweet, nutritive saccharide polymers that consist of D-glucose units linked primarily by alpha-1-4 bonds having a DE less than 20. It is prepared as a a white powder or concentrated solution by partial hydrolysis of corn starch with safe and suitable acids and/or enzymes. Maltodextrin is generally recognized as safe (GRAS) as a human food ingredient. Corn syrup solids, $(C_6H_{10}O_5)_n \bullet H_2O$, are defined as dried glucose syrup in which the reducing sugar content is 20. or higher. Corn syrup solids are also generally recognized as safe by the F.D.A.

In addition the composition of the invention contains about 0.1-15% of a seaweed derivative. The appropriate seaweed derivatives are salts or esters of alginic acid, carrageenans, or agar. Algin is the polysaccharide extracted from brown seaweed. It exists in seaweed as a form of alginic acid and its various salts. Derivatives of alginic acid and its salts are available from Kelco, Division of Merck & Co., Clark, N.J.

The various alginates are graded by their degree of polymerization. In general low molecular weight polymers give low viscosity aqueous solutions and high molecular weight polymers give viscous solutions. Salts or esters of alginic acid which are suitable include sodium alginate, ammonium alginate, propylene glycol alginate, potassium alginate, calcium alginate or blends of any of the above. Preferred are the salts of alginates, particularly sodium alginate.

The appropriate amount of hydrolyzed grain endproduct and seaweed derivative is mixed in about 20-95% water to yield a gel with a cream-like consistency. Example 1 sets forth various compositions suitable for masque application.

The hydrolyzed grain endproduct component, maltodextrin or corn syrup solids, is a macromolecule carbohydrate that can be highly soluble in water. At very high concentrations in aqueous solutions it demonstrates relatively low viscosity rendering it unsuitable for face masque consideration by itself. However, maltodextrin can provide the bulk and body required for adequate film formation. The alginate component, comprising alginic acid and/or its derivatives from seaweed, gives highly viscous aqueous solutions at considerably lower concentrations than maltodextrin. Alginates by themselves are unsuitable for specified face masque compositions. However, when combined with maltodextrin the alginate augments the maltodextrin by producing the thickening and thixotropic consistency needed for masque application. Surprising, both macromolecules are compatible in solution. After evaporation their combined film tends to plasticize more readily and provide unexpected and welcomed effects on the face. It rinses away freely and leaves the skin feeling soft, toned, and refreshed.

The essential face masque composition can be formulated for its many advantages and also to avoid many of the drawbacks present in other rinse-away masques. The masque cools the skin and acts astringently as it dries to a transparent film (if desired) on the face. It can be applied quickly and can dry rapidly, within 5 minutes or so. It is a convenient facial treatment because it deep cleans leaving the skin feeling smooth, the face feeling refreshed, toned, and young looking. It may be used in the daily routine just prior to facial makeup, or nightly, after makeup removal.

The preferred range of essential components in the composition of the invention are 5-60% maltodextrin, 1-6% alginate, and 40-85% water.

It is highly desirable to enhance the aesthetic potential of the face masque composition by adding one or more of a preservative, humectant, surfactant, fragrance, colorant, plasticizer, buffer, moisturizer, opacifier, or texturizer.

A wide variety of preservatives are suitable including but not limited to methyl paraben, propyl paraben, quaternium-15, EDTA, imidazolidinyl urea, sodium dehydroacetate, DMDM hydantoin, etc.

The humectants may be glycerin, urea, glycerin, collagen, butylene glycol, ethyl hexane diol, lactic acid, sodium lactate, orotic acid, sorbitol, sodium 2-pyrrolidone-5-carboxylate, polyethylene glycol, etc.

A wide variety of surfactants are suitable including but not limited to alkyl glycoside surfactants, other nonionic surfactants such as polysorbate 20, polysorbate 60, nonoxynol 12, octoxynol 9, oleamine oxide, stearamine oxide, cocodiethanol amide, polyethoxylated fatty amines, etc.

Suitable anionic surfactants include but are not limited to sodium lauryl sulfate, other salts of higher alkyl sulfates such as potassium lauryl sulfate; salts of alkyl ether sulfates such as polyoxyethylene triethanolamine lauryl sulfate, polyoxyethylene sodium lauryl sulfate; salts of alkyl ether sulfates such as polyoxyethylene triethanolamine lauryl sulfate or polyoxyethylene sodium lauryl sulfate; N-acyl sarcosinates; salts of higher fatty acid amide sulfonic acids; salts of phosphates such as polyoxyethylene sodium oleyl ether phosphate, or polyoxyethylene stearyl ether phosphate, etc.

Suitable cationic surfactants include but are not limited to, cetyl trimethylammonium chloride, stearylkonium chloride, tricetylammonium chloride, stearyl trimethylammonium chloride, or other alkyl trimethylammonium salts such as lauryl trimethylammonium chloride; alkyl pyridinium salts such as distearyl dimethyl ammonium dialkyl dimethyl ammonium chloride, cetyl pyridinium chloride, alkyl quaternary amonium salt, alkyl dimethyl benzyl ammonium salt, etc.

Amphoteric surfactants may also be used, for example cocoamphopropionate, soyamidopropyl betaine, tallow betaine, caproamphodiacetate, lauroamphodipropionate, etc.

Fragrances are also optional and include but are not limited to eucalyptol, balsam, herb, honey, floral, citrus, apple or menthol.

Plasticizers can include glycerine, propylene glycol, polyethylene glycol, ethoxylated lanolin alcohols, and various alkoxylated long chain alcohols, carboxylic acids and esters.

It is sometimes desireable to add solutions which buffer or regulate the pH of the masque composition. Appropriate pH regulators include acids, alkalis, and their salts including but not limited to salicylic acid, phosphoric acid, citric acid, sorbic acid, sodium hydroxide, ammonium hydroxide, etc.

Colorants will also impart a pleasant color to the face masque composition. Examples of suitable colorants include all of the FD&C colors approved for cosmetic use as well as, various inorganic pigments, reflective metal oxide micas, cholesteric liquid crystals, etc.

Moisturizers are very desireable additives also. A wide variety of moisturizing agents may be used, including but not limited to hyaluronic acid, aloe extract, mucopolysaccharides, royal jelly, methoxypropylgluconamide, hydrolyzed protein, allantoin, and so on.

Texturizers are desireable since they impart better texture to the skin. Suitable texturizers are methoxypropylgluconamide, fatty amine and quaternary ammonium salts, silicone derivatives such as dimethicone polyol, alkoxylated fatty alcohols & acids, cationic polymers, etc.

On some occasions it may be desired to enhance or impart opacifying agents to enhance a particular characteristic. One such known opacifying agent is insoluble apple pectin although many others are suitable.

In the preferred embodiment of the invention the masque composition contains 5-60% maltodextrin, 1-6% of a salt or ester of alginic acid and 40-85% water and may contain, in addition, one or more of the following optional components in the ranges set forth below:

| | |
|---|---|
| Moisturizer | 0.1-3.0% |
| Surfactant | 0.1-7.0% |
| Texturizer | 0.05-10% |
| Fragrance | 0.05-1.0% |
| Plasticizer | 0.1-2.0% |
| Preservative | 0.01-1.0% |
| Humectant | 0.1-1.0% |
| Opacifier | 0.1-10% |
| Buffer | 0.1-5% |
| Colorant | .05-15% |

The preferred face masque composition of the invention is set forth in Example 2 and additionally contains a surfactant, a texturizer, a fragrance and a preservative. The preferred texturizing agent is methoxypropylgluconamide which compound is described in U.S. patent application Ser. No. 184,858 which corresponds to Published European Patent Application 89107155.7 which is hereby incorporated by reference, and the preferred surfactant is an alkyl glycoside surfactant resulting in a composition having the following preferred ranges:

| | |
|---|---|
| Maltodextrin | 5-60% |
| Sodium Alginate | 2-6 |
| Methoxypropylgluconamide | 0.05-2.0 |
| Alkyl glycoside surfactant | 0.1-7.0 |
| Water | 40-85 |
| Fragrance | 0.5-1.0 |
| Preservative | 0.01-1.0 |

The invention is also directed to a method for treating human skin for improvement comprising administering to the facial skin a face masque composition comprised of about 1-70% of a hydrolyzed grain endproduct, about 0.1-15% of a seaweed derivative, and about 20-95% water.

The composition is evenly applied to the face. It dries to a transparent film in about 5-15 minutes. The face is then rinsed well with water to remove the masque. The face feels refreshed, clean, and toned.

The words "impart improved properties" or "treating human skin for improvement" means the treatment of skin by imparting moisture, refreshment, smoothness, texture, cleansing, firming, toning, cooling, tightening, and so on.

The invention will be further described in connection with the following examples which are set forth for the purposes of illustration only.

EXAMPLE 1

Maltodextrins of varying DE's were mixed with various grades of sodium alginate to yield compositions suitable for face masque application.

| | | |
|---|---|---|
| A. | Maltodextrin - DE 18 | 50.0 |
| | Sodium Alginate - (intermediate viscosity) | 3.5 |
| | Water | qs 100.0 |
| B. | Maltodextrin - DE 13 | 25.0 |
| | Sodium Alginate - (intermediate viscosity) | 3.5 |
| | Water | qs 100.0 |
| C. | Maltodextrin - DE 17 | 60.0 |
| | Sodium Alginate - (high viscosity) | 0.5 |
| | Water | qs 100.0 |
| D. | Maltodextrin - DE 5 | 5.0 |
| | Sodium Alginate - (high viscosity) | 1.0 |
| | Water | qs 100.0 |
| E. | Maltodextrin - DE 19 | 15.0 |
| | Sodium Alginate - (low viscosity) | 10.0 |
| | Water | qs 100.0 |

EXAMPLE 2

A face masque composition containing additional ingredients was made as follows. Note: all maltodextrin derivatives were obtained from Grain Processing Corporation, Muscatine, Iowa. All alginate derivatives were obtained from Kelco, Division of Merck & Co., Clark, N.J.

| | |
|---|---|
| Maltrin M-180 ® (Maltodextrin) | 25.0% |
| Methoxypropylgluconamide | 1.0 |
| Water | 69.35 |
| Alkyl glycoside surfactant (100%) | 0.6 |

| | |
|---|---|
| Kelgin F ® (Sodium Alginate) | 3.5 |
| Eucalyptol | 0.15 |
| Preservative | 0.4 |

Methoxypropylgluconamide is a special ingredient which acts as a texturizer. It is believed to reduce the layers of corneocytes in the skin which causes reduction in the thickness of the stratum corneum which in turn improves the flexibility and smoothness of the skin's surface. It also helps to alleviate dry skin conditions.

The Maltrin ® was dissolved with the methoxypropylgluconamide in water, the surfactant added and the preparation heated to 70° C. Sodium alginate was slowly added, dissolved, and followed by the remaining ingredients. This formulation was a clear gel with a creme-like consistency. When applied to the face as a thin clear film it dried in 5 minutes, producing an astringent effect on the skin. After rinse-off it left the skin feeling soft, looking rejuvinated and clean. The pH of the formulation was about 6.43.

EXAMPLE 3

A face masque composition was made as follows:

| | |
|---|---|
| Maltrin M-180 ® (Maltodextrin) | 50.0% |
| Kelgin F ® (Sodium Alginate) | 2.0 |
| Preservative | 0.2 |
| Glycerin | 0.5 |
| Alkyl glycoside surfactant (100%) | 1.8 |
| Eucalyptol | 0.15 |
| Water | 45.35 |

The Maltrin ® was dissolved in water and brought to 70° C. Glycerin and alkyl glycoside surfactant were added. Keeping the temperature at 70° C.±5° C., sodium alginate was slowly added to the vortex formed by mixer agitation. After adequate stirring to dissolve the sodium alginate with minimum air entrapment the eucalyptol and preservative were mixed in. Upon cooling the resulting solution was clear, slightly amber colored, and highly viscous. The solution was carefully filled into high density polyethylene tubes and the bottoms of the tubes were heatcrimp sealed. The product was applied to the face as a clear film. It filled in wrinkles and creases of the skin. After drying and hardening it was rinsed off to leave the face feeling refreshed, the skin soft.

The following formulations demonstrate further embodiments of the invention.

EXAMPLE 4

| | |
|---|---|
| Maltrin M-040 ® (Maltodextrin) | 12.0 |
| Kelcoloid HVF ® (Propylene Glycol Alginate) | 10.0 |
| Salicylic Acid | 0.1 |
| Polysorbate 20 | 0.5 |
| Preservative | 0.2 |
| Balsamic Fragrance | 0.1 |
| Reflective TiO$_2$/Fe$_2$O$_3$ coated mica | 0.2 |
| Water | qs 100.0 |

EXAMPLE 5

| | |
|---|---|
| Maltrin M-550 ® (Maltodextrin) | 25.0 |
| Kelmar ® (Potassium Alginate) | 6.0 |
| Hyaluronic Acid | 0.3 |

| | |
|---|---|
| Nonoxynol 12 | 1.0 |
| Aloe Extract | 1.0 |
| Preservative | 0.3 |
| Herbal Fragrance | 0.3 |
| FD&C Green #5 (2% aqueous) | 0.1 |
| Water | qs 100.0 |

EXAMPLE 6

| | |
|---|---|
| Maltrin M-180 ® (Maltodextrin) | 30.0 |
| Kelset (Sodium/Calcium Alginate) | 3.0 |
| Mucopolysaccharides | 0.4 |
| Royal Jelly | 0.1 |
| Preservative | 0.2 |
| Honey Fragrance | 0.3 |
| Octoxynol 9 | 0.9 |
| Water | qs 100.0 |

EXAMPLE 7

| | |
|---|---|
| Maltrin M-100 ® (Maltodextrin) | 20.0 |
| Maltrin M-040 ® (Maltodextrin) | 5.0 |
| Kelgin F (Sodium Alginate) | 3.5 |
| Cetyl trimethylammonium chloride | 0.1 |
| Sodium chloride | 2.5 |
| Polysorbate 60 | 0.3 |
| Lemon fragrance | 0.1 |
| Citrus extract | 0.5 |
| Preservative | 0.25 |
| Water | qs 100.0 |

Although the essential binary composition produces clear films on the face which have great advantage, the virtues of the physical properties of the inventive film should not restrict itself solely to clear orientation. The formulations below are not clear:

EXAMPLE 8

| | |
|---|---|
| Maltrin M-180 ® (Maltodextrin) | 20.0 |
| Maltrin M-050 ® (Maltodextrin) | 5.0 |
| Kelgin HV ® (Sodium Alginate) | 2.0 |
| Apple pectin | 5.0 |
| Dimethicone | 0.5 |
| Sodium lauryl sulfate | 0.4 |
| Apple fragrance | 0.5 |
| Preservative | 0.4 |
| Red colorant | 0.3 |
| Water | qs 100.0 |

EXAMPLE 9

| | |
|---|---|
| Maltrin M-150 ® (Maltodextrin) | 37.0 |
| Kelgin MV ® (Sodium Alginate) | 3.0 |
| Cholesteric liquid crystals | 10.0 |
| Menthol | 0.2 |
| Hydrolyzed protein | 0.2 |
| Alkyl glycoside surfactant | 2.0 |
| Polysorbate 20 | 3.0 |
| Preservative | 0.3 |
| Water | qs 100.0 |

EXAMPLE 10 IN VIVO EVALUATION

The face masque composition of Example 2 was evaluated in-situ in a test on twelve omen who regularly use rinse-away masques. Prior to testing the formulation was screened for safety and shown to be very mild to the skin and virtually non-irritating to the eyes.

The women were asked to apply a thin film of masque over their face after they had removed all makeup. The masque was allowed to dry and then rinsed away with warm water. The face was patted dry and makeup applied. A summary of the test results highlighted the following points:

All 12 panelists found the skin masque to apply acceptably.

Eleven out of 12 panelists found the masque to rinse acceptably.

All 12 panelists found the skin clean, soft and smooth.

Seven out of 12 panelists found the Eucalyptol odor unpleasant.

Eleven out of 12 panelists said they would purchase the product.

Most panelists volunteered the response that the product tightened the skin and was cooling. Some said that makeup was easier to apply after treatment.

What is claimed is:

1. A face masque composition used to impart improved properties to human skin consisting essentially of about 1-70% of maltodextrin, about 0.1-15% of a seaweed derivative selected from the group consisting of salts or esters of alginic acid, carrageenan, and agar, and about 20-95% water.

2. The composition of claim 1 wherein the seaweed derivative is a salt or ester of alginic acid.

3. The composition of claim 2 containing about 5-60% maltodextrin, 1-6% of a salt or ester of alginic acid and 40-85% water.

4. The composition of claim 3 wherein the salt or ester of alginic acid is sodium alginate, propylene glycol alginate, potassium alginate, ammonium alginate or calcium alginate.

5. The composition of claim 4 containing 0.01-1.0% of a fragrance selected from the group consisting of eucalyptol, balsam, honey, herbal, floral, apple, citrus and menthol.

6. The composition of claim 5 containing 0.05-15% of a colorant selected from the group consisting of reflective metal oxide mica, FD&C color, cholesteric liquid crystals, inorganic pigment or mixtures thereof.

7. A face masque composition used to impart improved propertiew to human skin comprising about 5-60% of maltodextrin, 1-6% sodium alginate, 0.05-2.0% methoxypropylgluconamide, 0.1-7% alkyl glucoside surfactant, 0.1-3.0% of a moisturizer selected from the group consisting of hyaluronic acid, aloe extract, mucopolysaccharides, royal jelly, hydrolyzed protein, or mixtures thereof, 0.1-1.0% of a fragrance selected from the group consisting of eucalyptol, balsam, honey, herbal, floral, apple citrus or menthol, 0.1-1.0% glycerine, 0.1-10% apple pectin, 0.05-5% of a buffer selected from the group consisting of phosphoric acid, sodium phosphate, citric acid, and ammonium phosphate, 0.05-15% of a colorant selected from the group consisting of reflective metal oxide mica, FD&C color, or inorganic pigment, 0.01% preservative and 40-85% water.

8. The composition of claim 7 containing about 25.0% maltodextrin, 1.0% methoxypropylgluconamide, 69.35% water, 0.6% alkyl glycoside surfactant, 3.5% sodium alginate, 0.15% fragrance and 0.4% preservative.

9. A method for treating human skin for improvement comprising administering to the skin a face masque composition consisting essentially of 1-70% maltodextrin, about 0.-15% of a seaweed derivative selected from the group consisting of salts or esters of alginic acid, carrageenan, and agar, and about 20-95% water.

* * * * *